US011925153B2

(12) United States Patent
Shur et al.

(10) Patent No.: US 11,925,153 B2
(45) Date of Patent: Mar. 12, 2024

(54) CONTROLLING LIGHT EXPOSURE OF LIGHT SENSITIVE OBJECT

(71) Applicant: Sensor Electronic Technology, Inc., Columbia, SC (US)

(72) Inventors: Michael Shur, Vienna, VA (US); Alexander Dobrinsky, Vienna, VA (US); Maxim S. Shatalov, Columbia, SC (US); Arthur Peter Barber, III, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 17/669,744

(22) Filed: Feb. 11, 2022

(65) Prior Publication Data

US 2022/0159912 A1    May 26, 2022

Related U.S. Application Data

(63) Continuation of application No. 17/101,245, filed on Nov. 23, 2020, now Pat. No. 11,246,266, which is a
(Continued)

(51) Int. Cl.
*A01G 7/04* (2006.01)
*A01G 9/20* (2006.01)
(Continued)

(52) U.S. Cl.
CPC .............. *A01G 7/045* (2013.01); *A01G 9/20* (2013.01); *A01G 22/00* (2018.02); *G01J 3/10* (2013.01);
(Continued)

(58) Field of Classification Search
CPC ..... A01G 7/045; G01J 3/10; G01J 3/42; G01J 3/4406; G01J 3/443; G01N 21/55
See application file for complete search history.

(56) References Cited

U.S. PATENT DOCUMENTS 7,553,456 B2    6/2009    Gaska et al.
8,277,734 B2    10/2012   Koudymov et al.
(Continued)

OTHER PUBLICATIONS

Bryant, M., U.S. Appl. No. 15/678,456, Notice of Allowance, dated Jul. 29, 2020, 9 pages.
(Continued)

*Primary Examiner* — David P Porta
*Assistant Examiner* — Casey Bryant
(74) *Attorney, Agent, or Firm* — LaBatt, LLC

(57) ABSTRACT

An approach for controlling light exposure of a light sensitive object is described. Aspects of this approach involve using a first set of radiation sources to irradiate the object with visible radiation and infrared radiation. A second set of radiation sources spot irradiate the object in a set of locations with a target ultraviolet radiation having a range of wavelengths. Radiation sensors detect radiation reflected from the object and environment condition sensors detect conditions of the environment in which the object is located during irradiation. A controller controls irradiation of the light sensitive object by the first and second set of radiation sources according to predetermined optimal irradiation settings specified for various environmental conditions. In addition, the controller adjusts irradiation settings of the first and second set of radiation sources as a function of measurements obtained by the various sensors.

20 Claims, 9 Drawing Sheets

Related U.S. Application Data continuation of application No. 15/678,456, filed on Aug. 16, 2017, now Pat. No. 10,842,081.

(60) Provisional application No. 62/382,216, filed on Aug. 31, 2016.

(51) Int. Cl.
| | |
|---|---|
| *A01G 22/00* | (2018.01) |
| *G01J 3/10* | (2006.01) |
| *G01J 3/42* | (2006.01) |
| *G01J 3/44* | (2006.01) |
| *G01J 3/443* | (2006.01) |
| *G01N 21/55* | (2014.01) |
| *G05B 15/02* | (2006.01) |

(52) U.S. Cl.
CPC .............. *G01J 3/42* (2013.01); *G01J 3/4406* (2013.01); *G01J 3/443* (2013.01); *G01N 21/55* (2013.01); *G05B 15/02* (2013.01); *G01J 2003/102* (2013.01); *Y02P 60/14* (2015.11)

(56) References Cited

U.S. PATENT DOCUMENTS

| | | | |
|---|---|---|---|
| 8,384,047 B2 | 2/2013 | Shur et al. | |
| 8,850,742 B2 | 10/2014 | Dube | |
| 9,034,271 B2 | 5/2015 | Shur et al. | |
| 9,179,703 B2 | 11/2015 | Shur et al. | |
| 9,550,004 B2 | 1/2017 | Smetona et al. | |
| 9,629,313 B1* | 4/2017 | Grossman | A01G 27/00 |
| 9,707,307 B2 | 7/2017 | Shur et al. | |
| 9,724,441 B2 | 8/2017 | Shur et al. | |
| 2010/0115830 A1 | 5/2010 | Dube | |
| 2011/0000807 A1* | 1/2011 | Snelten | A01G 9/249 |
| | | | 220/1.5 |
| 2014/0060094 A1* | 3/2014 | Shur | F25D 27/005 |
| | | | 422/186.3 |
| 2014/0060096 A1 | 3/2014 | Shur et al. | |
| 2014/0060104 A1 | 3/2014 | Shur et al. | |
| 2015/0165079 A1 | 6/2015 | Shur et al. | |
| 2015/0230409 A1* | 8/2015 | Nicole | A01G 9/14 |
| | | | 315/153 |
| 2016/0114186 A1 | 4/2016 | Dobrinsky et al. | |
| 2016/0345512 A1* | 12/2016 | Wargent | A01G 7/045 |
| 2017/0100495 A1 | 4/2017 | Shur et al. | |
| 2017/0100496 A1 | 4/2017 | Shur et al. | |
| 2017/0245527 A1 | 8/2017 | Dobrinsky et al. | |
| 2018/0028700 A1 | 2/2018 | Dobrinsky et al. | |
| 2018/0092308 A1 | 4/2018 | Barber, III et al. | |
| 2019/0098725 A1* | 3/2019 | Sadwick | F21S 2/00 |

OTHER PUBLICATIONS

Bryant, M., U.S. Appl. No. 15/678,456, Office Action 1, dated Mar. 25, 2020, 12 pages.

Bryant, M., U.S. Appl. No. 17/101,245, Notice of Allowance, dated Oct. 7, 2021, 7 pages.

* cited by examiner

CONTROLLING LIGHT EXPOSURE OF LIGHT SENSITIVE OBJECT

REFERENCE TO RELATED APPLICATIONS

The present patent application is a continuation of U.S. patent application Ser. No. 17/101,245, filed on 23 Nov. 2020, which is a continuation of U.S. patent application Ser. No. 15/678,456, filed on 16 Aug. 2017, now U.S. Pat. No. 10,842,081, issued 24 Nov. 2020, which claims the benefit of U.S. Provisional Application No. 62/382,216, filed on 31 Aug. 2016, all of which are hereby incorporated by reference.

TECHNICAL FIELD

The present invention relates generally to controlled lighting environments, and more particularly, to a smart lighting system that utilizes various sensors to detect radiation reflected from a light sensitive object, fluorescent radiation induced in the object, and/or conditions of the environment in which the object is located during irradiation, and a controller that controls the irradiation of the object according to predetermined optimal irradiation settings specified for various environmental conditions and feedback from the sensors.

BACKGROUND ART

A plant is one type of light sensitive object that can be grown in a controlled light environment. Growing plants under controlled conditions such as in greenhouses, growth cabinets or warehouses, generally entails monitoring the plant environment and controlling parameters such as light, water vapor pressure, temperature, $CO_2$ partial pressure, and air movement, in order to adjust the microclimate of the environment for optimizing growth and photosynthesis in an empirical manner. Plant attributes such as quantitative morphological, physiological and biochemical characteristics of at least a part of the plant may also be modulated during the monitoring of the plant environment and controlling of environment parameters.

Having the ability to determine the physiological condition of a plant or group of plants is useful in implementing photosynthetic responses into climate control algorithms or models that can be used in a controlled light environment. Optimization of photosynthesis of crops or plant material can be achieved through careful and planned manipulations of growth conditions based on in-situ monitoring of relevant photosynthetic processes. Relevant and short-term plant responses are involved in the definition of growth requirements not only through climate control, but also through the production processes, fertilizers, light quality, light intensity, and crop quality.

All these responses can ultimately affect economic returns. For example, the forestry industry replants millions of seedlings every year. These seedlings are initially grown in a controlled environment and are transplanted into the field during very specific and critical periods during seedling development. However, in the case of evergreen conifers it is difficult to determine by physical appearance alone when seedlings have reached the physiological state when they can be successfully transplanted outside. In addition, it can be difficult to determine from external plant appearances whether or not the light quality and intensity in a controlled environment is optimal for plant health and economic returns. Similarly, early determination of plant stress, effects of fertilizer and water regimes, grazing and effects of physical damage on the plant's vigor are difficult, if not impossible, to determine based on the external appearance of the plant. By the time the stress is physically apparent, the crop can be beyond a critical point of recovery.

To effectively control the climate, irrigation, nutrition, and light regime of greenhouse crops, in order to beneficially modulate and control growth and attributes of crops, sensors as well as models can be incorporated into a feed-forward/feedback component of a lighting system. Feed-forward controllers can use lamp light output to provide the necessary input for plant growth and have the capacity to anticipate the effects of disturbances on the greenhouse climate and in the light environment and take action within precisely set limits. Specific crop models, developed for individual crop species, can be based on data from sensors and used to estimate the benefits of changing growth regimes (e.g., spectral quality of the light source) to influence or modulate the outcome (e.g., flowering time). To this extent, the data obtained by the sensors can be combined with model-based algorithms in a lighting system to direct specific changes in light intensity and/or quality, influencing the plant's growth processes or attributes.

SUMMARY OF THE INVENTION

This Summary Of The Invention introduces a selection of certain concepts in a brief form that are further described below in the Detailed Description Of The Invention. It is not intended to exclusively identify key features or essential features of the claimed subject matter set forth in the Claims, nor is it intended as an aid in determining the scope of the claimed subject matter.

Aspects of the present invention are directed to a lighting system that incorporates optimal irradiation settings to irradiate a light sensitive object under a variety of environmental conditions, sensors to detect radiation reflected from the object and/or conditions from the environment in which the object is located during irradiation, and a controller that controls the irradiation of the object according to the optimal irradiation settings specified and feedback from the sensors. In this manner, the irradiation of the light sensitive object can be optimized to attain desired characteristics.

Various radiation sources can be used to irradiate the light sensitive object. In one embodiment, a set of visible light sources and infrared sources can irradiate the object over a range of wavelength. For example, the visible light sources can include a dark blue visible light source operating in a wavelength ranging from 440 nm to 450 nm, a blue visible light source operating at a peak wavelength of 470 nm and a full width half max ranging from 5 nm to 10 nm, a green visible light source operating in a wavelength ranging from 525 nm to 540 nm, a red visible light source operating in a wavelength ranging from 620 nm to 640 nm, a red visible light source operating at a peak wavelength of 660 nm and a full width half max ranging from 5 nm to 10 nm, while the infrared sources operate in a wavelength ranging from 725 nm to 740 nm.

A plurality of ultraviolet radiation sources can complement the visible light sources and infrared sources in the irradiation of the object. In one embodiment, the ultraviolet radiation sources can be used for spot irradiation of the object. The ultraviolet radiation sources can operate at different peak wavelengths and irradiate the object at different locations with relatively uniform radiation. In one embodiment, more than one of the ultraviolet radiation sources can irradiate a common location of the object. To this extent, the ultraviolet radiation sources can irradiate the common location at different intensities of radiation.

In one embodiment, the light sensitive object can include a living organism, such as plant, where the various radiation sources can be used to irradiate parts of the plant, such as leaves, branches, trunks, roots, nodes, and buds. In an embodiment where a plant is the light sensitive object that is irradiated by radiation sources, the sensors can include one or more of a temperature sensor, a humidity sensor, a $CO_2$ sensor, a water sensor, a nutrient sensor, a fluorescent sensor, and a radiation sensor.

The controller can receive measurements from the sensor(s) to detect changes imparted to the plant by the radiation sources. The controller can analyze the data associated with the irradiation by the radiation sources and the data associated with environmental conditions surrounding the light sensitive object. In one embodiment, the data associated with the irradiation can include intensity, dosage, duration, wavelength, type of radiation, and pattern, while the environmental conditions can include temperature, humidity, presence of $CO_2$, and water. The controller can use this information to detect changes in the plant that include changes in size, shape, color, and temperature.

The controller can also use the information from the sensors to control a multitude of plant growth parameters by adjusting settings of the irradiation. In one embodiment, the plant growth parameters can include an amount of water provided to the plant, air temperature at a location of the plant, an amount of nutrients provided to the plant, and an amount of pesticides applied to the plant.

The controller can control the irradiation of the plant in this manner during different periods of plant growth. In one embodiment, the different periods can include a plant seedling period, a plant development period, a plant maturity period, plant blooming period, and a plant fruition period. The controller can be configured to receive measurements from the sensors at various times of the day during each of the different periods of plant growth. In one embodiment, the controller can direct the radiation sources to irradiate the plant according to a predetermined irradiation pattern. For example, the predetermined irradiation pattern can include a first irradiation by ultraviolet radiation sources, followed by second irradiation by visible light sources, and a third irradiation by fluorescent radiation sources.

The predetermined optimal irradiation settings specified for various environmental conditions can include a multitude of settings for the radiation sources. For example, settings can include the type, the wavelength, the intensity, the dosage, the duration, the pattern, and the frequency, of radiation emitted from the radiation sources for the plant during different periods of plant growth. In one embodiment, the predetermined optimal irradiation settings can be specified for different parts of the plant. In one embodiment, the predetermined optimal irradiation settings can be based on samples of plants that have been irradiated and samples of plants that were not irradiated. The settings based on samples of plants that have been irradiated can be derived from an analysis performed on locations of the plant that received focused irradiation and regions of the plant that did not receive irradiation. In one embodiment, the locations of the plant that received focused irradiation can receive fluorescent radiation while the regions of the plant without irradiation do not receive any of the fluorescent radiation. In this example, the analysis on the locations can include a fluorescent analysis to determine the effect that the fluorescent radiation has on formation of flavonoids in the plant for a specific period of plant growth under a variety of environmental conditions.

In one embodiment, the predetermined optimal irradiation settings can include a range of acceptable intensity radiation values over a time duration that are absorbable by the plant and that contribute to production of flavonoids and antioxidants within the plant without damaging plant cells. In another embodiment, the settings can further include a schedule specifying a time frame that the range of acceptable intensity radiation values are appropriate for use during each of the different periods of plant growth. The predetermined optimal irradiation settings and the schedule can be derived from ultraviolet plant absorption curves formed for the plant that show absorption of ultraviolet radiation for varying amounts of intensity over time.

In one embodiment, the predetermined optimal irradiation settings can be derived from a fluorescent analysis of the plant that has undergone irradiation through ultraviolet radiation and visible light radiation. For example, the fluorescent analysis can include obtaining fluorescent signals from the plant in response to irradiation by visible light radiation, obtaining fluorescent signals from the plant in response to irradiation by ultraviolet radiation, plotting a ratio of the fluorescent signals from the visible light radiation to the fluorescent signals from the ultraviolet radiation as a function of wavelength, and ascertaining values in the ratio of the fluorescent signals that contribute to production of flavonoids and antioxidants within the plant. In one embodiment, a peak value in the ratio of the fluorescent signals can be indicative of an optimal wavelength for irradiating the plant.

The predetermined optimal irradiation settings can also be derived by irradiating a set of locations on the plant with different ultraviolet radiation sources. In one embodiment, each of the different ultraviolet radiation sources can irradiate a respective location with multiple wavelengths of ultraviolet radiation. In this manner, each of the different ultraviolet radiation sources can irradiate a respective location with ultraviolet radiation, such that each location can receive a different wavelength of the ultraviolet radiation. Fluorescent signals can then be obtained from each of the locations after irradiation of the different wavelengths of the ultraviolet radiation. The controller can use the fluorescent signals from each of the locations to determine a presence of a first chemical component on the surface of the plant that is indicative of a chemical modification and a second chemical component on the surface of the plant that is indicative of a newly formed chemical material relating to flavonoid and antioxidant production.

In another embodiment, the predetermined optimal irradiation settings can be derived by irradiating a set of locations on the plant with a single ultraviolet radiation source such that each location receives a different wavelength of the ultraviolet radiation from the single ultraviolet radiation source. Fluorescent signals can then be obtained from the plant in response to irradiation by the ultraviolet radiation. The set of locations on the plant can then be irradiated with a visible light source after ultraviolet radiation. Fluorescent signals can then be obtained from the plant in response to irradiation by the visible light source. A ratio of the fluorescent signals from the visible light radiation to the fluorescent signals from the ultraviolet radiation can then be determined as a function of wavelength. Values in the ratio of the fluorescent signals that contribute to growth of the plant can then be ascertained.

The predetermined optimal irradiation settings can further be derived by irradiating a set of locations on the plant with a set of different ultraviolet radiation sources. In one embodiment, each of the different ultraviolet radiation sources can irradiate a respective location with a different intensity and duration of ultraviolet radiation.

In another embodiment, the predetermined optimal irradiation settings can be derived from absorption spectra obtained at regions in the plant that contribute to flavonoid and antioxidant production and absorption spectra obtained at other regions in the plant. For example, the controller can determine an optimal wavelength of radiation that balances a peak in the absorption spectra of the regions in the plant that contribute to flavonoid production with any penalty or cost that the peak wavelength will have in the absorption spectra in other regions of the plant can be adversely effected by that amount of radiation.

A first aspect of the invention provides a light exposure control system for irradiating an object having a light sensitive surface, comprising: a first set of radiation sources configured to irradiate the object with visible radiation and infrared radiation; a second set of radiation sources configured to spot irradiate the object in a set of locations with ultraviolet radiation having a range of wavelengths; a radiation sensor configured to detect radiation reflected from the object; a plurality of environmental condition sensors that detect conditions of the environment in which the object is located during irradiation by the first and second set of radiation sources; and a controller configured to control irradiation of the light sensitive object by the first and second set of radiation sources according to a plurality of predetermined optimal irradiation settings specified for various environmental conditions, the controller adjusting irradiation settings of the first and second set of radiation sources as a function of fluorescent measurements obtained by the radiation sensor for at least two wavelengths, and the environmental conditions detected by the plurality of environmental condition sensors.

A second aspect of the invention provides a light exposure control system for irradiating a plant, comprising: a set of visible light and infrared radiation sources configured to irradiate a surface of the plant with visible radiation and infrared radiation; a set of ultraviolet radiation sources configured to spot irradiate the surface of the plant in a set of locations with a target ultraviolet radiation having a range of wavelengths; a radiation sensor configured to detect radiation reflected from the surface of the plant including visible radiation, ultraviolet radiation and fluorescent radiation; a plurality of environmental condition sensors that detect conditions of the environment in which the plant is located during irradiation by the set of visible light and infrared radiation sources and the set of ultraviolet radiation sources; and a controller configured to control irradiation of the surface of the plant by the set of visible light and infrared radiation sources and the set of ultraviolet radiation sources according to a plurality of predetermined optimal irradiation settings specified for various environmental conditions, wherein the controller directs the set of ultraviolet radiation sources to irradiate the set of locations on the surface of the plant with a first fluorescent excitation of radiation having a distinct wavelength of emitted radiation at a predetermined intensity and duration, and at a second fluorescent excitation of radiation having a wavelength of emitted radiation at a predetermined intensity and duration that is different from the first fluorescent excitation of radiation, the controller receiving fluorescence measurements from locations experiencing the first and second fluorescent excitations and locations unexposed to the first and second fluorescent excitations, the controller adjusting the irradiation settings of the set of visible light and infrared radiation sources and the set of ultraviolet radiation sources as a function of the fluorescence measurements.

A third aspect of the invention provides a method, comprising: irradiating a light sensitive object with visible radiation and infrared radiation; spot irradiating the light sensitive object in a set of locations with ultraviolet radiation having a range of wavelengths; detecting radiation reflected from the light sensitive object; detecting conditions of the environment in which the light sensitive object is located during the irradiation and spot irradiation; and controlling the irradiation and spot irradiation of the light sensitive object according to a plurality of predetermined optimal irradiation settings specified for various environmental conditions, the controlling including adjusting irradiation settings as a function of fluorescent measurements obtained for at least two wavelengths and the environment conditions.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
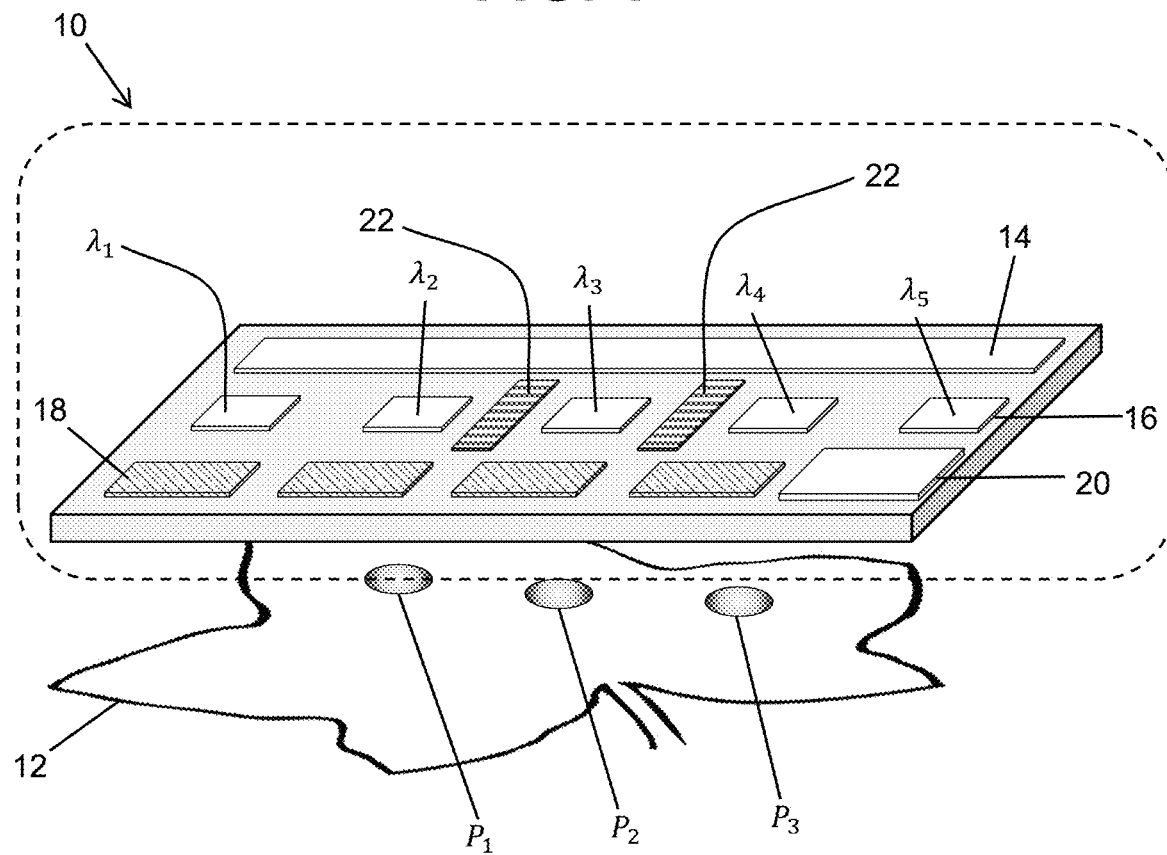
FIG. 1 shows a schematic of a light exposure control system for irradiating a light sensitive object such as a plant according to an embodiment.

As indicated above, aspects of the present invention are directed to a lighting system that incorporates predetermined optimal irradiation settings to irradiate a light sensitive object under a variety of environmental conditions, sensors to detect radiation reflected from the object and/or conditions from the environment in which the object is located during irradiation, and a controller that controls the irradiation of the object according to the predetermined optimal irradiation settings and feedback from the sensors.

Although the description that follows is directed to a plant, various embodiments of the present invention are suitable for use with any light sensitive object where it is desirable to irradiate a surface of the object to alter chemical and/or biological processes internal to the object in order to impart certain physiological responses. Examples of other light sensitive objects that are suitable for use with a lighting system that incorporates concepts of the various embodiments described herein can include, but are not limited to, living organisms such as humans and animals. In an embodiment, the present invention can be incorporated to affect material that undergoes a chemical reaction under radiation, such as an ultraviolet curable ink.

The various embodiments for controlling light exposure of a light sensitive object with a lighting system described herein can include a number of components (some of which may be optional) that facilitate the control of light exposure. These components and the functions that each can perform are described below in more detail. The components and actions can include any now known or later developed approaches that can facilitate implementation of the concepts and configurations of the various embodiments described herein.

As used herein, controlling light exposure of a light sensitive object means controlling a dose, type, angle, location, extent, and/or the like, of any radiation of light energy directed over at least some of a surface of the sensitive object. Generally, controlling light exposure of a light sensitive object can entail changing the intensity of the light, the wavelength of the light, the intensity distribution pattern, and/or the like, over a surface.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The description that follows may use other terminology herein for the purpose of describing particular embodiments only, and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It is further understood that the terms "comprises," "comprising," "includes," "including," "has," "have," and "having" when used in this specification, specify the presence of stated features, integers, steps, operations, elements, and/or components, but do not preclude the presence or addition of one or more other features, integers, steps, operations, elements, components, and/or groups thereof.

Turning to the drawings, FIG. 1 shows a schematic of a light exposure control system 10 for irradiating a light sensitive object 12, such as a plant, according to an embodiment. As used herein, a plant can include any one of a vast number of organisms within the biological kingdom Plantae. In general, a plant includes species that are considered of limited motility and generally manufacture their own food. A non-exhaustive list of plants can include, but are not limited to, vegetables, flowers, trees, forbs, shrubs, grasses, vines, ferns, and mosses. The light exposure control system 10 can include a first set of radiation sources 14 configured to irradiate the object with visible radiation and infrared radiation. The radiation sources 14 can include a set of visible light sources and infrared sources. Examples of visible light sources can include, but are not limited to, incandescent, fluorescent, laser, solid state, and/or the like, light sources that emit radiation having a wavelength at least partially in a range of 400 nm to 700 nm, while infrared sources can include, but are not limited to, blackbody, solid state, and/or the like, light sources that emit radiation having a wavelength at least partially in a range of 700 nm to 1 mm.

In one embodiment, the radiation sources 14 can include an array of a set of light emitting diodes (LEDs) operating in a blue, green, red, as well as an infrared range. The visible set of LEDs in the array can be operated to provide a sufficient intensity of light to allow for plant growth, while the infrared set of LEDs in the array can be operated to provide heating, regulate stem growth and flowering response, and/or the like. In one embodiment, the set of visible light sources and infrared sources can be configured to irradiate the plant according to a schedule that follows the amount of daylight and darkness in a given day of a year. That is, the set of visible light sources and infrared sources are operational to irradiate the plant during daylight hours and inoperative during nighttime hours of the given day of the year (which may differ from the actual day of the year).

The set of visible light sources and infrared sources can include a variety of sources that operate over a wide range of wavelengths. Generally, the set of visible light sources and infrared sources can irradiate an entirety of the surface of the light sensitive object 12 with a wavelength that ranges from 430 nm to 800 nm. In one embodiment, the set of visible light sources can include a dark blue visible light source operating in a wavelength ranging from 440 nm to 450 nm, a blue visible light source operating at a peak wavelength of 470 nm and a full width half maximum ranging from 5 nm to 10 nm, a green visible light source operating in a wavelength ranging from 525 nm to 540 nm, a red visible light source operating in a wavelength ranging from 620 nm to 640 nm, a red visible light source operating at a peak wavelength of 660 nm and a full width half maximum ranging from 5 nm to 10 nm, while the infrared sources can operate in a wavelength ranging from 725 nm to 740 nm. It is assumed that for these values, the peak wavelength is defined to within 1-5 nanometers. A set of these visible light sources and infrared sources that are configured to operate with the aforementioned wavelengths is beneficial because these spectra ranges are known to promote plant growth and plant fruit formation. In one embodiment, the visible light sources can irradiate a surface of the light sensitive object 12 with a wavelength that ranges from 430 nm to 560 nm. In another embodiment, the visible light sources can irradiate a surface of the light sensitive object 12 with a wavelength that ranges from 600 nm to 800 nm.

It is understood that the radiation sources 14 can include other radiation sources in addition to, or in place of, the set of visible light sources and infrared sources. For example, fluorescent lights, high pressure sodium lights, or metal halide lamps, and any other high intensity discharge lamps that are typically employed for growth of plants can be used with or in place of the set of visible light sources and infrared sources.

The light exposure control system 10 can further include a second set of radiation sources 16 configured to spot irradiate the object 12 in a set of locations with a target radiation having a range of wavelengths. These locations can include specific locations or regions of the object that can have a need for supplemental irradiation beyond the irradiation provided by the first set of radiation sources 14. Generally, each of the radiation sources 16 is capable of producing a spot of radiation at a distance from a light fixture. In this scenario of FIG. 1, the light fixture is the light exposure control system 10 itself, with the distance being a typical distance at which the system is installed. These distances can range from a few centimeters to a meter. As used herein, irradiation of a location defines a region of the object 12 that is impinged by radiation, wherein the intensity of radiation deposited at the boundary of the region is at most 10% of the intensity of light deposited at the center of the region. It is understood that the position of irradiated locations can be adjusted to result in separate locations over the surface of the object 12, wherein separate means that the intensity of radiation between the locations is no larger than 10% of the intensity in the center of the locations. In addition, these locations of irradiation can be designed to have relatively uniform radiation, with radiation intensity varying through the location of no more than several times between any two points within the location.

In one embodiment, the radiation sources 16 can include an ultraviolet radiation source. The ultraviolet radiation source can comprise any combination of one or more ultraviolet radiation emitter. Examples of an ultraviolet radiation emitter can include, but are not limited to, high intensity ultraviolet lamps (e.g., high intensity mercury lamps), discharge lamps, ultraviolet LEDs, super luminescent LEDs, laser diodes, and/or the like. In one embodiment, the ultraviolet radiation source can include a set of LEDs manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the ultraviolet radiation source can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures can include, but are not limited to, a wave guide, a plurality of ultraviolet fibers, each of which terminates at an opening, a diffuser, and/or the like.

The set of radiation sources 16 can include a set of ultraviolet radiation sources each operating at a different peak wavelength ($\lambda$). As shown in FIG. 1, the set of ultraviolet radiation sources 16 can include a source operating at a peak wavelength of $\lambda_1$, a source operating at a peak wavelength of $\lambda_2$, a source operating at a peak wavelength of $\lambda_3$, a source operating at a peak wavelength of $\lambda_4$, and a source operating at a peak wavelength of $\lambda_5$. The number of ultraviolet radiation sources depicted with the set of radiation sources 16 is only illustrative, and thus, it is understood that any number of ultraviolet radiation sources can be used. In one embodiment, each of the ultraviolet radiation sources can irradiate a different location of the object 12. It is understood for clarity that FIG. 1 shows three locations (e.g., $P_1$, $P_2$, $P_3$) although it is understood that the plant could have other locations that are irradiated with the ultraviolet radiation sources. In one embodiment, the ultraviolet radiation sources can irradiate each location with relatively uniform radiation. In another embodiment, more than one ultraviolet radiation source can be used to irradiate a single location on the object, with each irradiating the common location at a different intensity of radiation.

Each of the ultraviolet radiation sources can be configured to irradiate radiation at a specific wavelength selected from a range extending from 250 nm to 360 nm. In general, for adequate optimization of the spot irradiation that is provided by the ultraviolet radiation sources, the wavelength range can be selected to be significantly narrower. For instance, the wavelength range can extend from 270 nm to 320 nm, and in some cases, depending on the optimization target, the range can extend from 280 nm to 300 nm, or from 260 nm to 280 nm. In one embodiment, the ultraviolet radiation sources can have a peak wavelength that ranges from 270 nm to 300 nm. In another embodiment, the ultraviolet radiation sources can have a peak wavelength of 295 nm with a full width half maximum of 10 nm.

In order to facilitate the spot irradiation performed by the ultraviolet radiation sources 16, a set of reflective optical elements can be used to focus the ultraviolet radiation to locations on the object 12. In one embodiment, each optical element can be configured to focus ultraviolet radiation emitted from one of the ultraviolet radiation sources to a respective location on the object 12. Examples of optical elements that can be used in conjunction with the ultraviolet radiation sources include, but are not limited to, a lens and/or a set of lenses.

Although the set of visible light and infrared sources 14 and the ultraviolet radiation sources 16 are depicted in FIG. 1 as separate components, it is understood that these radiation sources can be combined in a single component. In one embodiment, regardless of whether the sources are part of a single component or multiple components, the radiation sources can include a dark blue visible light source operating in a wavelength ranging from 440 nm to 450 nm, a blue visible light source operating at a peak wavelength of 470 nm and a full width half maximum ranging from 5 nm to 10 nm, a green visible light source operating in a wavelength ranging from 525 nm to 540 nm, a red visible light source operating in a wavelength ranging from 620 nm to 640 nm, a red visible light source operating at a peak wavelength of 660 nm and a full width half maximum ranging from 5 nm to 10 nm, while the infrared sources can operate in a wavelength ranging from 725 nm to 740 nm. In addition, this embodiment can include a UVA source operating at a peak wavelength of 365 nm with a full width half maximum ranging from 5 nm to 10 nm, and a UVB source operating in a wavelength that ranges from 280 nm to 300 nm.

In another embodiment, the visible light, infrared and ultraviolet radiation sources can be implemented as a grow lamp fixture with adjustable intensities that are configured to operate in various modes. For example, the grow lamp fixture can include a dark blue source that is 10% of intensity of the grow lamp fixture; a blue source that is 5% of the intensity of the grow lamp fixture; a green source that is 5% of the intensity of the grow lamp fixture; a red source that is 20% of intensity of the grow lamp fixture; a red source that is 50% of the intensity of the grow lamp fixture; an infrared source that is 5% of the grow lamp fixture; a UVA source that is 5% of the intensity of the grow lamp fixture; and a UVB source that is 5% of the intensity of the grow lamp fixture.

The light exposure control system 10 can further include a plurality of sensors 18 configured to measure a plurality of conditions associated with irradiating the light sensitive object 12. FIG. 1 shows that the sensors 18 includes four sensors, however it is understood that this amount is only for illustrative purposes. Those skilled in the art will appreciate that the type and amount of sensors 18 can vary, and will depend on what the light sensitive object 12 comprises and the application or reason for irradiating the object. In an embodiment in which the light sensitive object 12 is a plant and the application of the light exposure control system 10 is to facilitate growth of the plant, the sensors 18 can include a set of environmental condition sensors that detect conditions of the environment in which the plant is located during irradiation by the first set of radiation sources 14 and the second set of radiation sources 16. In one embodiment, the environmental condition sensors can include a temperature sensor, a humidity sensor, a $CO_2$ sensor, a water sensor, and a nutrient sensor. For example, a temperature sensor can measure the temperature surrounding the plant, the humidity sensor can measure the humidity surrounding the plant, the $CO_2$ sensor can measure the $CO_2$ levels surrounding the plant, a water sensor can measure an amount of water surrounding the plant or on the leaves, branches, etc., while the nutrient sensor can measure the presence of various nutrients (e.g., flavonoids) in the plant based on plant leaf reflectivity data. These environmental condition sensors are only illustrative of a few possibilities, and it is understood that other sensors can be used to obtain environmental conditions related to the growth of a plant or plants in a controlled environment such as greenhouses, warehouses, etc. For example, an air pressure sensor can measure the air pressure of the location in which the plant is located, and an air movement sensor can measure the air speed in close proximity to the plant.

The sensors 18 can include other sensors in addition to the environmental condition sensors. For example, the set of sensors 18 can include sensors that measure operational data associated with the irradiation by the first set of radiation sources 14 and the second set of radiation sources 16. In one embodiment, the sensors 18 can include at least one of a radiation sensor to detect radiation reflected from the surface of the object 12. For example, the set of sensors 18 can include a fluorescent radiation sensor to detect the fluorescent radiation induced in the surface of the object by the first set of radiation sources 14 and the second set of radiation sources 16. Other examples of sensors that can be used in the light exposure control system 10 can include, but are not limited to, visible light sensors, chemical sensors, a visible camera, etc.

The light exposure control system 10 can further include a controller 20 to control the irradiation of the light sensitive object 12 by the first set of radiation sources 14 and the second set of radiation sources 16 according to a plurality of predetermined optimal irradiation settings specified for various environmental conditions in which the object is located. In addition, the controller 20 can adjust the irradiation settings of the first set of radiation sources 14 and the second set of radiation sources 16 as a function of measurements obtained by the plurality of sensors 18.

In one embodiment, the controller 20 can detect changes imparted to the light sensitive object 12 from the radiation sources as a function of data fed back from the sensors 18. In particular, the controller 20 can detect the changes as a function of the data associated with the irradiation by the first set of radiation sources 14 and the second set of radiation sources 16, and the data associated with environmental conditions surrounding the light sensitive object 12. In one embodiment, the data associated with the irradiation can include the intensity, dosage, duration, wavelength, the type of radiation emitted from the first set of radiation sources 14 and the second set of radiation sources 16, and the frequency of irradiation. In embodiments in which the light sensitive object 12 is a plant and the light exposure control system 10 is used to facilitate the growth of the plant, the environmental conditions can include temperature, humidity, and the presence of $CO_2$ and/or water. In embodiments in which the light sensitive object 12 is a living organism such as a person or an animal and the light exposure control system 10 is used to apply a medical treatment, the environmental conditions can include various vital signs such as, for example, blood pressure, heart rate, temperature, pulse, humidity of the skin, and reflectivity of the skin. In embodiments in which the light sensitive object 12 is a plant, the changes that can be detected by the controller 20 can include, but are not limited to, changes in size, shape, color, temperature and overall harvest yield. In embodiments in which the light sensitive object 12 is a human or an animal, the changes that can be detected by the controller 20 can include, but are not limited to, color changes of the human/animal skin, visual changes occurring over the surface of the human/animal skin (such as curing of the wounds, changes in the scarring tissue), etc.

The controller 20 can detect the changes imparted to the light sensitive object 12 from the data obtained from the sensors 18 using any solution. For example, in embodiments in which the light sensitive object 12 is a plant and the light exposure control system 10 is used to facilitate the growth of the plant, the controller 20 can ascertain changes in size, shape, color, temperature and overall harvest yield of the plant using visual, fluorescent and/or infrared sensors and sources. In an embodiment, using visual means can include a source of visible radiation, and a camera sensitive to visible radiation. The camera can acquire image data of an object at a first instance of time and at a later instance of time under similar lighting conditions, assuming that the plant is not moved or otherwise physically altered. The controller 20 can compare the image data to determine changes in size, shape, color, and/or overall volume of the plant. The changes in size and volume can provide information regarding an overall harvest yield, while the changes in color can provide information regarding a health and nutrient content of the plant. Fluorescent radiation sources and fluorescence sensors can be utilized to acquire information regarding changes of the plant surface related to accumulation of flavonoids at the plant surface. Infrared radiation and infrared sensors can be utilized to acquire information regarding the temperature of the plant surface. Similar to the visual source and camera, the fluorescent and infrared sources and sensors can acquire data at set instances of time, which the controller 20 can compare at such different instances.

In embodiments in which the light sensitive object 12 is a human or an animal in a medical treatment scenario, the controller 20 can ascertain changes to the patient skin such as skin color and/or skin condition using visual, fluorescent, and/or infrared sensors and sources in the same manner as described in conjunction with the plant surface analysis.

The controller 20 can adjust the irradiation settings of the first set of radiation sources 14 and the second set of radiation sources 16 as a function of the feedback signals from the sensors using any solution. In this manner, the controller can cause the first set of radiation sources 14 and the second set of radiation sources 16 to direct a particular type of radiation to the applicable surface or area of the object 12. In general, the controller 20 can adjust the operation of the first set of radiation sources 14 and the second set of radiation sources 16 by specifying certain operating parameters that can include, but are not limited to, wavelength, intensity, dosage, duration, pattern and frequency. As an example, the controller 20 can control the radiation sources 14, 16 to operate at a target wavelength and intensity for a duration that is designed to attain a certain effect (e.g., increase production of a certain flavonoid and/or antioxidants).

In other embodiments, the controller 20 can include a timer with switches and/or the like, to manage the duration that the first set of radiation sources 14 and the second set of radiation sources 16 are on for a particular application. To this extent, use of the timer can ensure that radiation including spot irradiation is applied to the surface of the object 12 for that duration (e.g., a dosage timer). In an embodiment in which the object 12 is a plant and the light exposure control system 10 is used to facilitate the growth of the plant, the timer can be used to coordinate the active operation of the radiation sources to correspond with the amount of daylight in a particular day, and inactivate the sources during nighttime hours. In one embodiment, the controller 20 operating in conjunction with the timer can manage the amount of time that the ultraviolet radiation sources radiate in the UV-A range versus the UV-B range. The duration and frequency treatment that the ultraviolet radiation sources are utilized can depend on detected condition signals provided to the controller 20 by any of the sensors 18.

The controller 20 can also be used turn off the first set of radiation sources 14 and the second set of radiation sources 16 upon any detected conditions provided by any of the sensors 18. For example, the controller 20 can be configured to interrupt the operation of the first set of radiation sources 14 and the second set of radiation sources 16 in response to receiving temperature signals from a temperature sensor and determining that the temperature of the air surrounding the object 12 has exceeded a maximum temperature which is not beneficial for receiving any particular type of radiation.

In one embodiment, the controller 20 can include a memory storage capable of recording the various data obtained from the sensors 18. To this extent, the controller can retrieve the data for further analysis and optimization of the irradiation settings. Further details of the analyses and optimization of the settings, as well as the control of various parameters that are performed by the controller are presented below.

In one embodiment, the controller 20 can also include a wireless transmitter and receiver that is configured to communicate with a remote location via Wi-Fi, BLUETOOTH, and/or the like. As used herein, a remote location is a location that is apart from the light exposure control system 10. For example, a remote computer can be used to transmit operational instructions to the wireless transmitter and receiver. The operational instructions can be used to program functions performed and managed by the controller 20. In another embodiment, the wireless transmitter and receiver can transmit data calculations (e.g., changes), data from the sensors to the remote computer, to facilitate further use of the light exposure control system 10 with the object 12.

In one embodiment, the controller 20 can include an input component and an output component to allow a user to interact with the light exposure control system 10 and to receive information regarding the object 12 and the treatment thereto with the radiation sources. In one embodiment, the input component can permit a user to adjust at least one of the aforementioned plurality of operating parameters. This can include making adjustments during the operation of the radiation sources 14, 16 and/or prior to initiating a treatment. In one embodiment, the input component can include a set of buttons and/or a touch screen to enable a user to specify various input selections regarding the operating parameters. In one embodiment, the output component can include a visual display for providing status information on the irradiation of the object (e.g., time remaining, humidity, presence of water, or the like), status information of the object (e.g., changes in shape and size), a simple visual indicator that displays whether irradiation is underway (e.g., an illuminated light), or if the irradiation is over (e.g., absence of an illuminated light).

Although not illustrated in FIG. 1 for clarity, the light exposure control system 10 can include a power source that is configured to power the first set of radiation sources 14 and the second set of radiation sources 16, the sensors 18 and the controller 20. In one embodiment, the power source can take the form of one or more batteries, a vibration power generator that can generate power based on magnetic inducted oscillations or stresses developed on a piezoelectric crystal. In another embodiment, the power source can include a super capacitor that is rechargeable. Other power components that are suitable for use as the power source can include a mechanical energy to electrical energy converter such as a piezoelectric crystal, and a rechargeable device.

The aforementioned components of the light exposure control system 10 are only illustrative of one possible configuration. It is understood that the light exposure control system 10 can utilize other components in addition to, or in place of those described above. These additional components can perform similar functions to those described above or different ones. The type of additional components and functionalities that are performed will depend on the type of light sensitive object and the result that is desired through irradiation by the radiation sources.

In one embodiment, the light exposure control system 10 can include at least one fluorescent radiation source 22. For example, the light exposure control system 10 can include a set of fluorescent radiation sources 22 each configured to expose a location on the light sensitive object 12 with fluorescent excitation. The fluorescent radiation sources 22 can include, but are not limited to, visible and ultraviolet sources (e.g., visible and ultraviolet fluorescent sources). Although the fluorescent radiation sources 22 are depicted in FIG. 1 as separate components, it is understood that these sources of fluorescent radiation can be part of the first set of radiation sources 14 and the second set of radiation sources 16. In this embodiment, at least one of the sensors 18 can include a fluorescent signal sensor to measure an amount of fluorescence at each location on the light sensitive object 12 that is exposed to fluorescent excitation. In one embodiment, the controller 20 can compare the fluorescence at each location to an amount of fluorescence at a region of the light sensitive object 12 that is unexposed to the fluorescent excitation emitted from the fluorescent radiation source 22. The controller 20 can use this comparison in fluorescence to determine changes in the surface due to fluorescence radiation source 22. Based on this comparison as well as other data obtained from the sensors 18, the controller 20 can adjust the irradiation of the object by any of the radiation sources 14, 16, 22. With regard to the operation of the fluorescent radiation source 22, the controller 20 can modify the wavelength, intensity, dosage, duration, pattern of radiation that irradiates the set of locations on a surface of the object 12, and/or the frequency of irradiation.

The visible light radiation sources, the ultraviolet radiation sources, and the fluorescent radiation sources can be operates in conjunction with each other to irradiate the surface of the light sensitive object 12 including a set of locations along the surface in a variety of patterns. In one embodiment, the ultraviolet radiation sources can irradiate a set of locations at a peak wavelength of 295 nm with a full width half maximum of 10 nm. In another embodiment, the ultraviolet radiation sources can irradiate the set of locations at peak wavelength that ranges from 270 nm to 300 nm. The irradiation of the locations in these embodiments can be characterized by a first characteristic diameter. Next, the visible light radiation sources can irradiate the entire surface of the expose with a visible light at a wavelength that range from 430 nm to 800 nm. The fluorescent radiation sources 22 can then irradiate the set of locations on the surface of the light sensitive object 12 with a first fluorescent excitation of radiation having a distinct wavelength of emitted radiation at a predetermined intensity and duration, resulting in the locations having a second characteristic diameter.

In one embodiment, the first fluorescent excitation of radiation can be in an ultraviolet range having a wavelength that ranges from 260 nm to 280 nm. In another embodiment, the first fluorescent excitation of radiation can be in an ultraviolet range having a wavelength that ranges from 280 nm to 300 nm. The controller 20 can then direct the fluorescent radiation sources to irradiate the set of locations on the surface of the light sensitive object 12 with a second fluorescent excitation of radiation having a wavelength of emitted radiation at a predetermined intensity and duration that is different from the first fluorescent excitation of radiation. In one embodiment, the second fluorescent excitation of radiation can be in a visible light range having a wavelength that ranges from 430 nm to 560 nm. In another embodiment, the second fluorescent excitation of radiation can be in a visible light range having a wavelength that ranges from 600 nm to 800 nm.

It is understood that the analysis can be performed as the controller 20 receives the fluorescent signals, or the analysis can be performed after all of the signals have been received and recorded in a storage (memory, database, etc.). In addition, it is understood that the set of locations and the surface of the object 12 can be irradiated according to different patterns. For example, the ultraviolet radiation sources can be used to generate different fluorescent excitation signals.

The fluorescent radiation sources 22 and the fluorescent sensors can operate in various configurations to ensure that detected fluorescent signals are differentiated from the fluorescent sources inducing such fluorescent signals. For example, the fluorescent radiation sources 22 and the fluorescent sensors can operate in a pulsed regime to ensure that the fluorescent signals are differentiated from the sources inducing such fluorescent signals. Alternatively, the sources of fluorescent signals can be filtered by wavelength to result in a clear collection of fluorescent signals from the surface of the light sensitive object 12. It is understood that any timing for delivering the radiation to the light sensitive surface and collecting the fluorescent signal from the surface is possible. In an embodiment, the time resolved fluorescence can be employed, wherein the fluorescent radiation source can operate in a pulsed regime and the fluorescent data can be collected as the fluorescent signal is decaying. This method is known also as a transient fluorescent response, as it allows for determining the lifetime of fluorescence, and possibly a phase delay between an excitation and a response which can lead to a particular sensing signature for the light sensitive surface 12.

Figure 2:
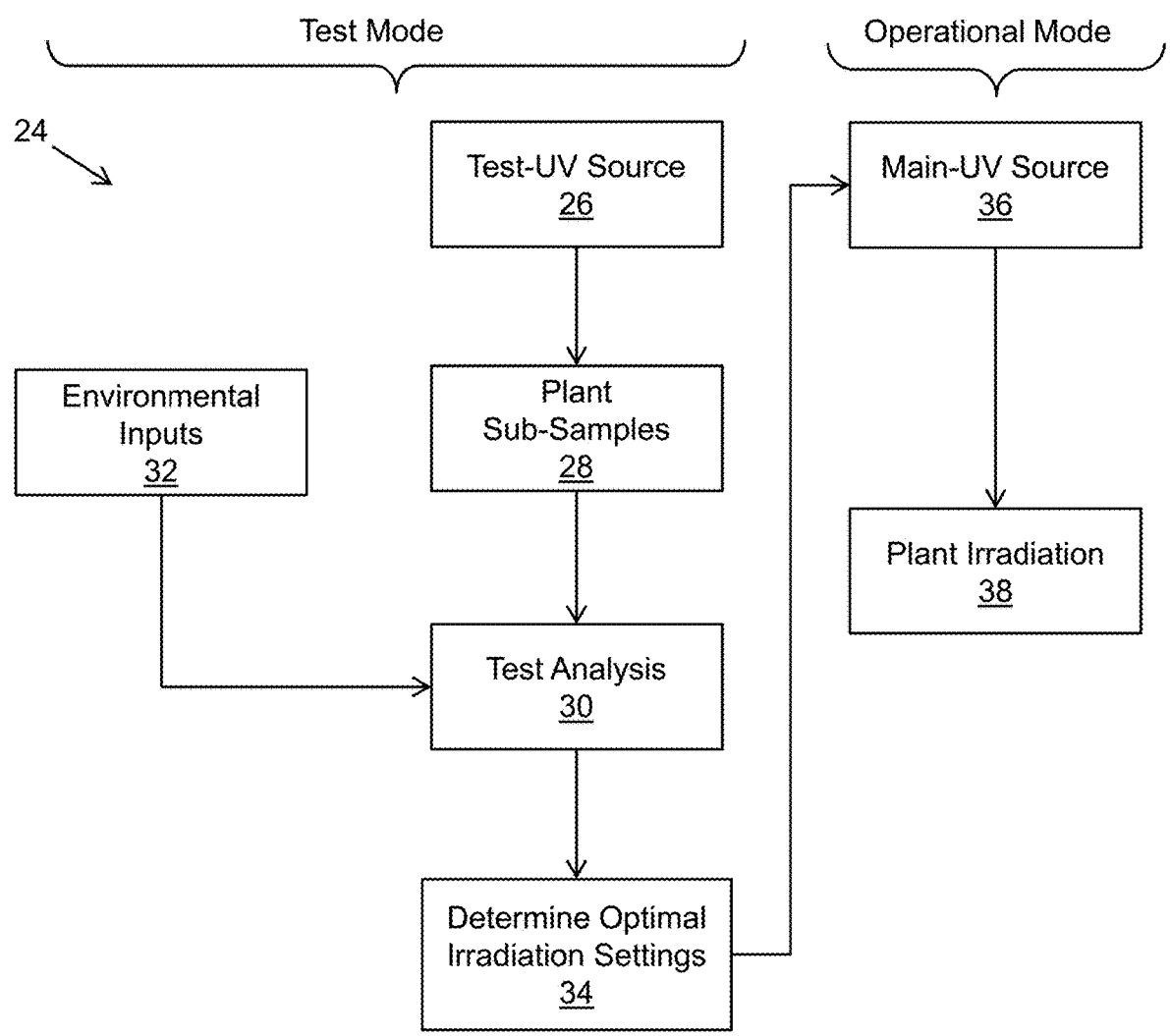
FIG. 2 shows a flow chart describing the use of a light exposure control system described herein in a test mode to determine optimal irradiation settings and in an operational treatment mode using the settings to irradiate a light sensitive object such as a plant according to an embodiment.

FIG. 2 shows a flow chart 24 describing the use of the light exposure control system 10 (FIG. 1) in a test mode to determine optimal irradiation settings, and in an operational treatment mode using the settings to irradiate a light sensitive object, such as a plant, according to an embodiment. In the test mode, the ultraviolet radiation sources from the set of radiation sources 16 of the light exposure control system 10 can be used at 26 to irradiate a set of plant sub-samples 28. The ultraviolet radiation sources can irradiate multiple plant sub-samples 28 at a variety of wavelengths, intensities, dosages, durations, and/or patterns including partial surface coverage, full surface coverage, and spot irradiation. In one embodiment, the ultraviolet radiation sources can irradiate a first set of plant sub-samples 28 using a first peak wavelength and a second set of plant sub-samples 28 using a second peak wavelength. In an embodiment, the first set of plant sub-samples 28 can be irradiated by a first set of peak wavelengths administered one after another at a first set of intervals, whereas the second set of plant sub-samples 28 can be irradiated by a second set of peak wavelengths administered one after another at a second set of intervals. In an embodiment, the variables that control irradiation of the first and second set of plant sub-samples 28 can include duration of radiation and intensity of radiation for each peak wavelength administered. In an embodiment, several peak wavelengths can be administered at the same time. In some embodiments, it may be desirable to have some plant sub-samples not be irradiated by the ultraviolet radiation sources.

After irradiating the plant sub-samples 28 with ultraviolet radiation, the controller 20 of the light exposure system can perform a test analysis 30 on the data obtained from the sensors 18 (FIG. 1) during the irradiation. The test analysis can be based on locations of the plants that received focused irradiation and regions of the plant that did not receive spot irradiation, as well as any regions that did not receive any radiation at all. As shown in FIG. 2, the test analysis 30 can be performed according to a set of environmental inputs 32 that have an effect on the growth of the plant sub-samples 28. Examples of the environmental inputs 32 can include, but are not limited to, humidity of the ambient, $CO_2$ content of the ambient, and temperature. In an embodiment, the nutrient content in the plant environment (water) can be controlled, as an additional parameter of the environment.

The test analysis 30 can use the data obtained from the sensors 18 during the irradiation of ultraviolet radiation and the specified environmental inputs to ascertain plant growth, plant health and a presence of nutrients (for example flavonoids) within plant leafs. In one embodiment, the test analysis 30 can include an ultraviolet irradiation analysis to assess fluorescent properties of the plant. The ultraviolet irradiation analysis can entail radiating a plant with visible radiation and measuring a fluorescent signal at the first instance of time, then radiating a plant with ultraviolet signal at a peak wavelength corresponding to flavonoid absorption, and measuring fluorescent signal from such response. The analysis can include measuring two fluorescent signal intensities to ascertain the flavonoid content of the plant. The ratio from the fluorescent signals can be tabulated against plant flavonoid content and the tabulated values can be used for determining flavonoid content within the plant.

The fluorescent analysis can be performed at different times from the ultraviolet irradiation analysis. To this extent, a time dependent reaction of a surface of the plant that is sensitive to the irradiation by the ultraviolet radiation sources and the fluorescent sources can be determined. In one embodiment, the fluorescent analysis can include a first fluorescent analysis that is performed prior to irradiation of the plant by the ultraviolet radiation sources. A second fluorescent analysis can be performed after the irradiation of the plant by the ultraviolet radiation sources. The controller 20 can then compare the results from the first fluorescent analysis to the second fluorescent analysis. The controller 20 uses the comparison of the results from the first fluorescent analysis to the second fluorescent analysis to determine the changes due to radiation. In an embodiment, the ultraviolet radiation can also be used to reduce the amount of mildew over the leaves of the plant, and the fluorescent analysis can test the presence of mildew after irradiation. The ultraviolet irradiation analysis and the fluorescent analysis process can be repeated several times depending on the set of environmental conditions. In addition, the ultraviolet irradiation analysis and the fluorescent analysis can be performed on a day-to-day basis. The controller 20 can then store the results from the ultraviolet irradiation analysis and the fluorescent analysis, and any assessments made therefrom for further processing and control of operational parameters.

The controller 20 can use the results from the test analysis at 30 to determine the optimal irradiation settings at 34 for irradiating a plant with the light exposure control system under various environmental conditions. These optimal irradiation settings can include, but are not limited to, the type of radiation, the wavelength, the intensity, the dosage, the duration, and/or the frequency of radiation to be emitted from the radiation sources 14, 16. The optimal irradiation settings can also be specified for types of plants during different periods of plant growth. The different periods of plant growth can include, but are not limited to, a plant seedling period, a plant development period, a plant maturity period, a plant blooming period, and a plant fruition period. In addition, the optimal irradiation settings can also be specified for different parts of the plant. For example, certain parts of the leaves or sections of the plants such as the plant trunk or roots can have vastly different irradiation conditions. As a result, the various sections of the plant may require spot irradiation, different types of radiation, different intensities to facilitate growth or attain certain flavonoids, chlorophylls, or the like.

With the optimal irradiation settings determined, the light exposure control system 10 can be used as a recipe in an operational mode to treat a plant or plants according to these settings for plant growth. To this extent the first set of radiation sources 14 can be used to irradiate the plants with visible light and infrared light, while the second set of radiation sources 16 can be used at 36 to provide the main ultraviolet irradiation. This enables the ultraviolet radiation sources to irradiate the plants at 38 with the optimal irradiation settings over the different periods of plant growth under a variety of environment conditions. In one embodiment, the light exposure control system can be implemented in a controlled environment like a greenhouse and can be used to globally irradiate the plants in the greenhouse in accordance with the optimal irradiation settings. It is understood that the use of the light exposure control system and the predetermined optimal settings in a greenhouse scenario is only one example, and that it is applicable to growth of plants in different settings and/or irradiation of other light sensitive objects for any of various purposes.

Figure 3:
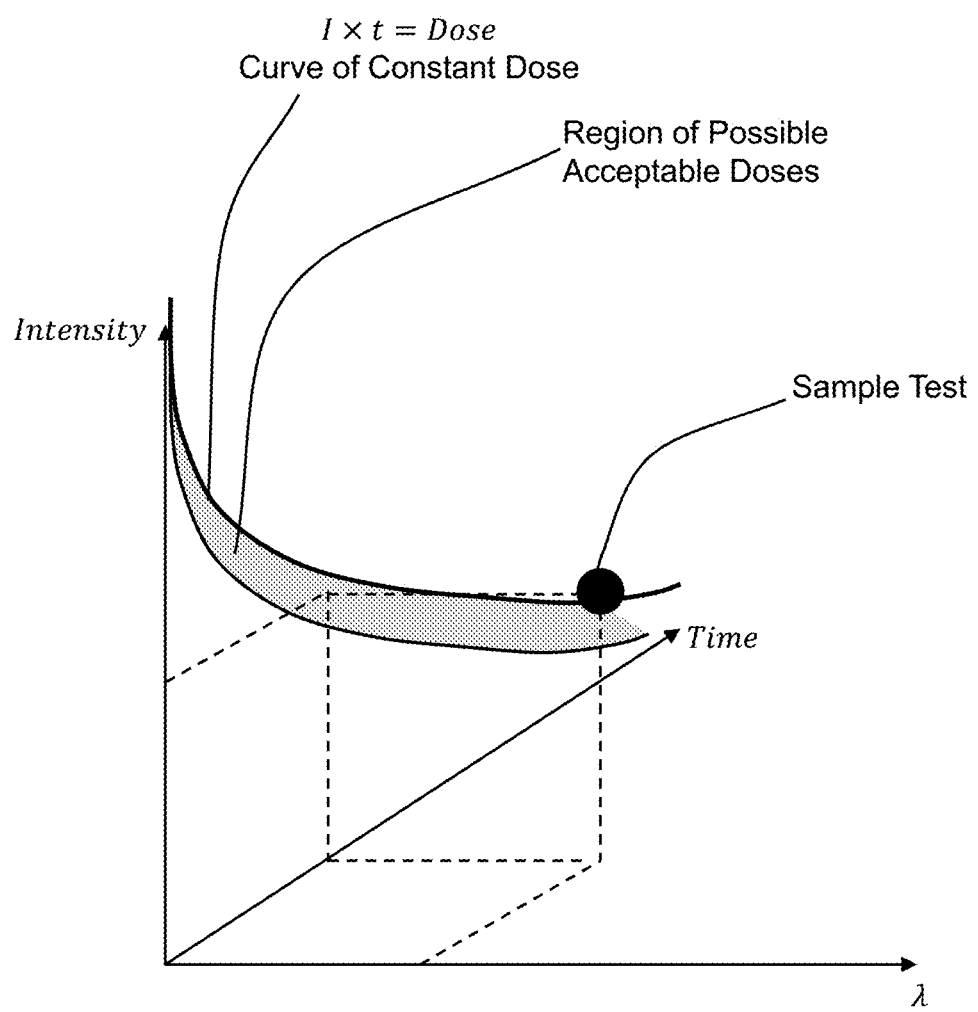
FIG. 3 illustrates a parameter space of optimal irradiation settings in relation to settings used in a sample test irradiation of a plant during the test mode depicted in FIG. 2 according to an embodiment.

FIG. 3 illustrates a parameter space of optimal irradiation settings in relation to settings used in a sample test irradiation of a plant from the test mode depicted in FIG. 2 according to an embodiment. As shown in FIG. 3, the parameter space can include wavelength, intensity, dose, and time, which can include the duration and frequency of the irradiation. It is understood that the time parameter does not have to be periodic and can be based on any time schedule. FIG. 3 depicts the optimal irradiation settings as the region of possible acceptable doses. This region represents the space of acceptable radiation dosages, intensities and wavelengths generated from the radiation sources that can irradiate a plant to effectuate desirable plant growth under various environmental conditions over different periods of plant growth. In general, it is understood that a certain radiation dose in this space that is administered in the operational treatment mode will be bound by a minimal and maximum value. This same dose can be administered in a short high intensity burst of radiation or in prolonged low intensity periods of radiation. To determine the best possible set of optimal settings, the test mode would need to scan a set of points in the parameter space obtained from the test samples. For clarity, FIG. 3 only shows one sample test, however it is understood that data from multiple tests would be obtained to ascertain a range of acceptable values that can be administered in an operational treatment mode.

Figure 4:
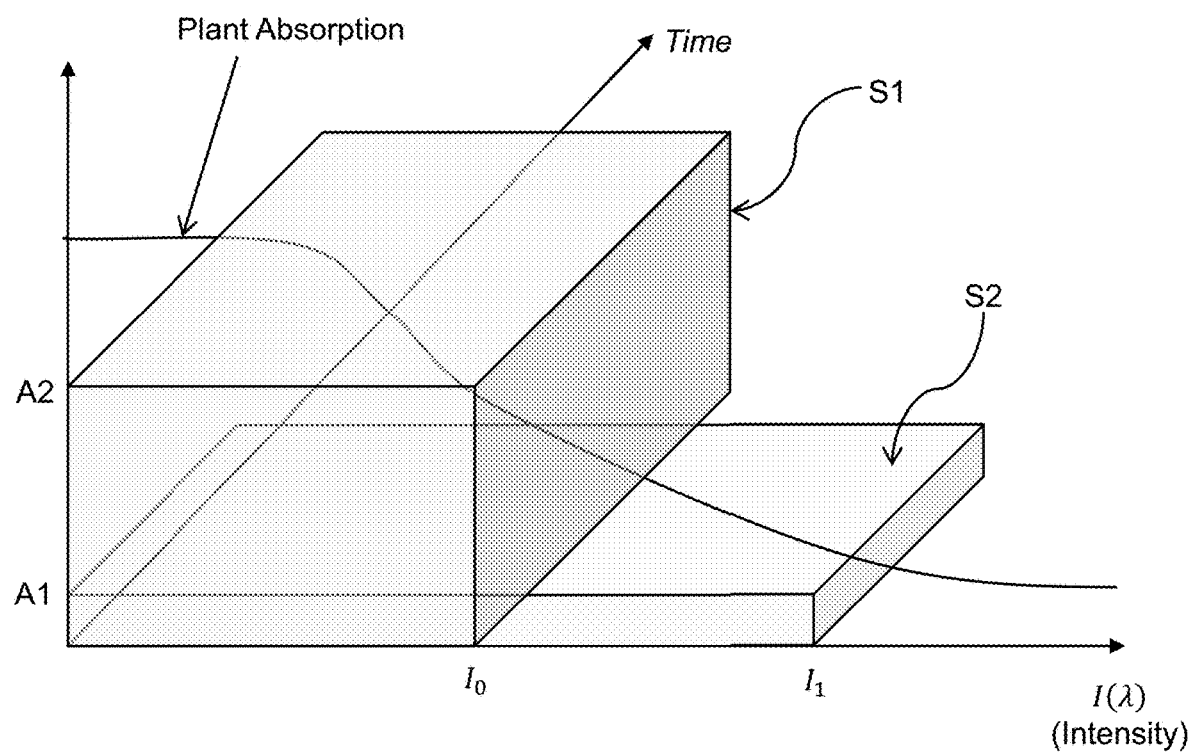
FIG. 4 illustrates an example of the effect that different intensity of radiation values can have on the absorption of the radiation in a light sensitive object over time according to an embodiment.

FIG. 4 illustrates an example of the effect that different intensity of radiation values can have on the absorption of the radiation in a light sensitive object such as a plant over time according to an embodiment. In general, the plant absorption of ultraviolet radiation can depend on the intensity of the ultraviolet radiation. For example, consider an ultraviolet sensing protein found in plants such as an ultraviolet-B resistance 8 (UVR8), also known as ultraviolet-B receptor UVR8. A plant that is irradiated with ultraviolet radiation will typically be absorbed at the UVR8, while other ultraviolet photons can be absorbed by plant tissue cells. Generally, for high intensity radiation sources, the absorption by the UVR8 will be saturated and the absorption of the plant tissue cells will be increased. Typically, absorption of the UVR8 is important component for production of flavonoids and antioxidants within a plant. As a result, it is sometimes preferable to radiate the plant for possibly longer times at a lower ultraviolet intensity to increase absorption effects.

FIG. 4 shows a possible plant absorption curve with each box S1 and S2 corresponding to a dose of radiation delivered to a plant. In general, the dose represented by box S1 is preferred over the dose represented by box S2 because it takes more time to deliver dose S1, and it requires significantly less intensity of radiation. In addition, a high intensity of radiation such as that associated with dose S2, can damage the plant cells that do not contribute to the production of flavonoids or antioxidants within the plant.

Plant absorption curves such as the one depicted in FIG. 4 can be used to determine a schedule for irradiating a plant. In one embodiment, the data obtained from the test mode, in which a multitude of plant samples are irradiated to ascertain optimal irradiation settings, can be used to generate ultraviolet absorption curves. Generally, such absorption curves can be obtained prior to optimizing the irradiation schedule, and can be measured separately from the other data obtained during the test mode. In one embodiment, the controller 20 can use the ultraviolet absorption curves as an initial data point for determining a set of possible irradiation intensities for plant treatment that can result in an adequate does of ultraviolet radiation delivered to the plant.

Figure 5:
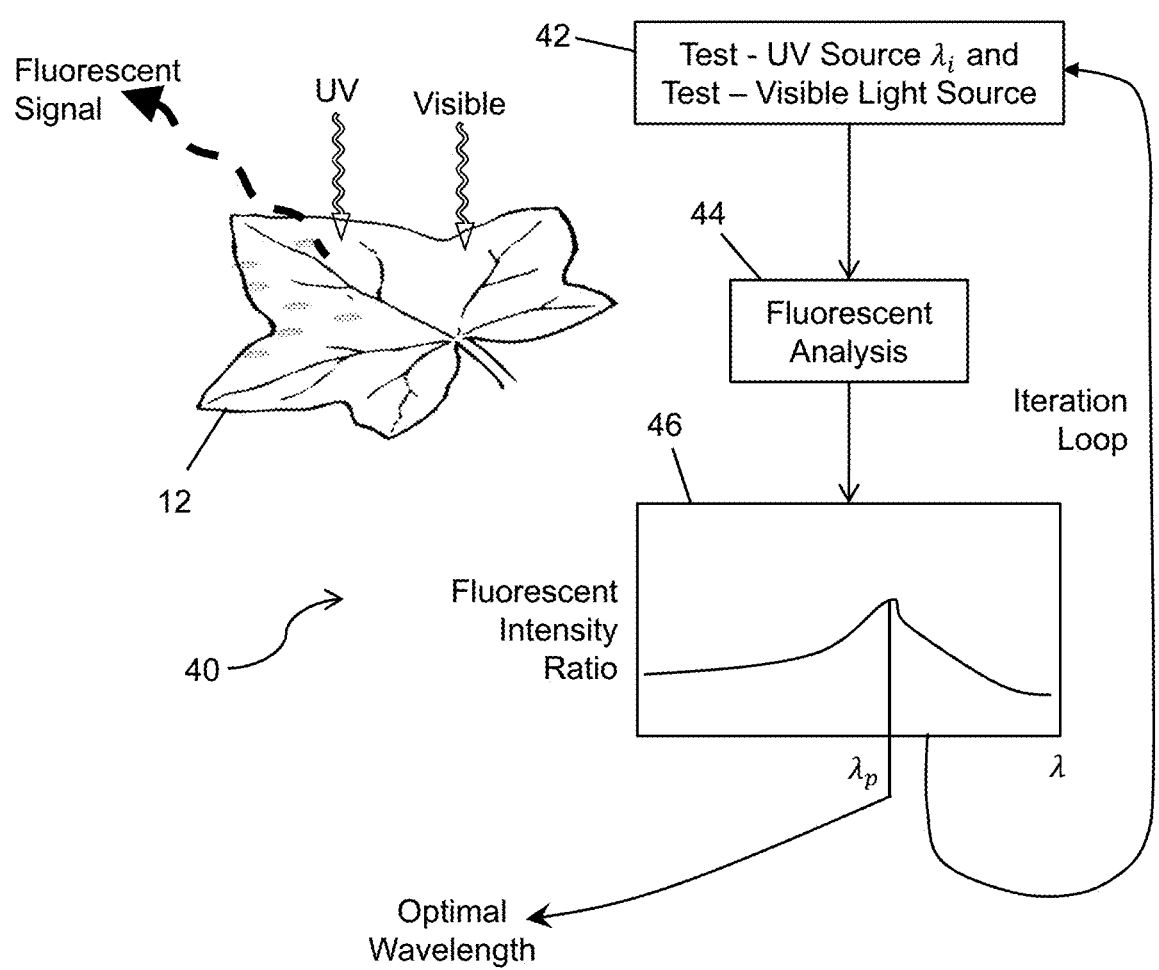
FIG. 5 shows a flow chart describing a test mode according to another embodiment that implements a fluorescent analysis to determine the optimal irradiation settings for use with a light exposure control system in an operational treatment mode of a light sensitive object such as a plant.

FIG. 5 shows a flow chart 40 describing a test mode according to another embodiment that implements a fluorescent analysis to determine the optimal irradiation settings for use with a light exposure control system described herein in an operational treatment mode of a light sensitive object such as a plant. In this embodiment, the test samples (e.g., the plants 12) are irradiated with the visible radiation sources and the ultraviolet radiation sources at 42. For example, the first set of radiation sources 14 (FIG. 1) can irradiate the plants 12 with visible light radiation at a visible light wavelength that results in a peak fluorescence. Such a wavelength can be established by first irradiating plant by a set peak wavelengths in the range of 400-700 nm and choosing the one with the peak fluorescence. The second set of radiation sources 16 (FIG. 1) can irradiate the plants 12 with ultraviolet radiation at a wavelength $\lambda_i$ and chosen in a wavelength range that is absorbed by flavonoids. Such a wavelength can be in the range of 285-300 nm for example, and $\lambda_i$ can represent ten equally spaced peak wavelengths in the aforementioned range.

The controller 20 (FIG. 1) can perform a fluorescent analysis at 44 in order to determine the flavonoid content in a plant. In one embodiment, the fluorescent analysis includes obtaining fluorescent signals from the plant 12 after being irradiated with the visible light radiation. In addition, fluorescent signals from the plant are obtained after being irradiated with the ultraviolet radiation. The controller 22 can use these signals to plot a ratio of the fluorescent intensity signals from the visible light radiation to the fluorescent signals from the ultraviolet radiation at 46 after compiling enough data from multiple irradiations of the plant 12 through different wavelengths, intensities, dosages, and/or duration. The plot of the fluorescent intensity signals as depicted in FIG. 5 is a function of wavelength $\lambda$.

The plot of the fluorescent intensity signals can be used to ascertain a variety of information that pertains to the growth of the plant under a variety of environmental conditions for different periods of plant growth. For example, large values in the fluorescent signal ratio is an indication that there is a considerable presence of flavonoids within the plant that are associated with the fulfillment of multiple functions (e.g., pigmentation, inhibit disease activity, etc.), and are generally responsible for health and nutritional benefits associated with many fruits and vegetables. In one embodiment, the controller 22 can use these values that are an indication of a considerable presence of flavonoids to determine a range of acceptable intensity radiation values over a time duration that are absorbable by the plant and that contribute to production of flavonoids. In addition, the peak value of the wavelength ($\lambda_p$) in the plot of the ratio of the fluorescent signals can be used as the optimal wavelength for the settings specified in the operational treatment mode because such a wavelength corresponds to a maximum flavonoid absorption, and results in a largest signal-to-noise ratio. Such a wavelength allows for more accurate prediction of flavonoid content. In addition, the choice of wavelength can determine the type of flavonoid that can be present in the proximity of the leaf surface.

Figure 6:
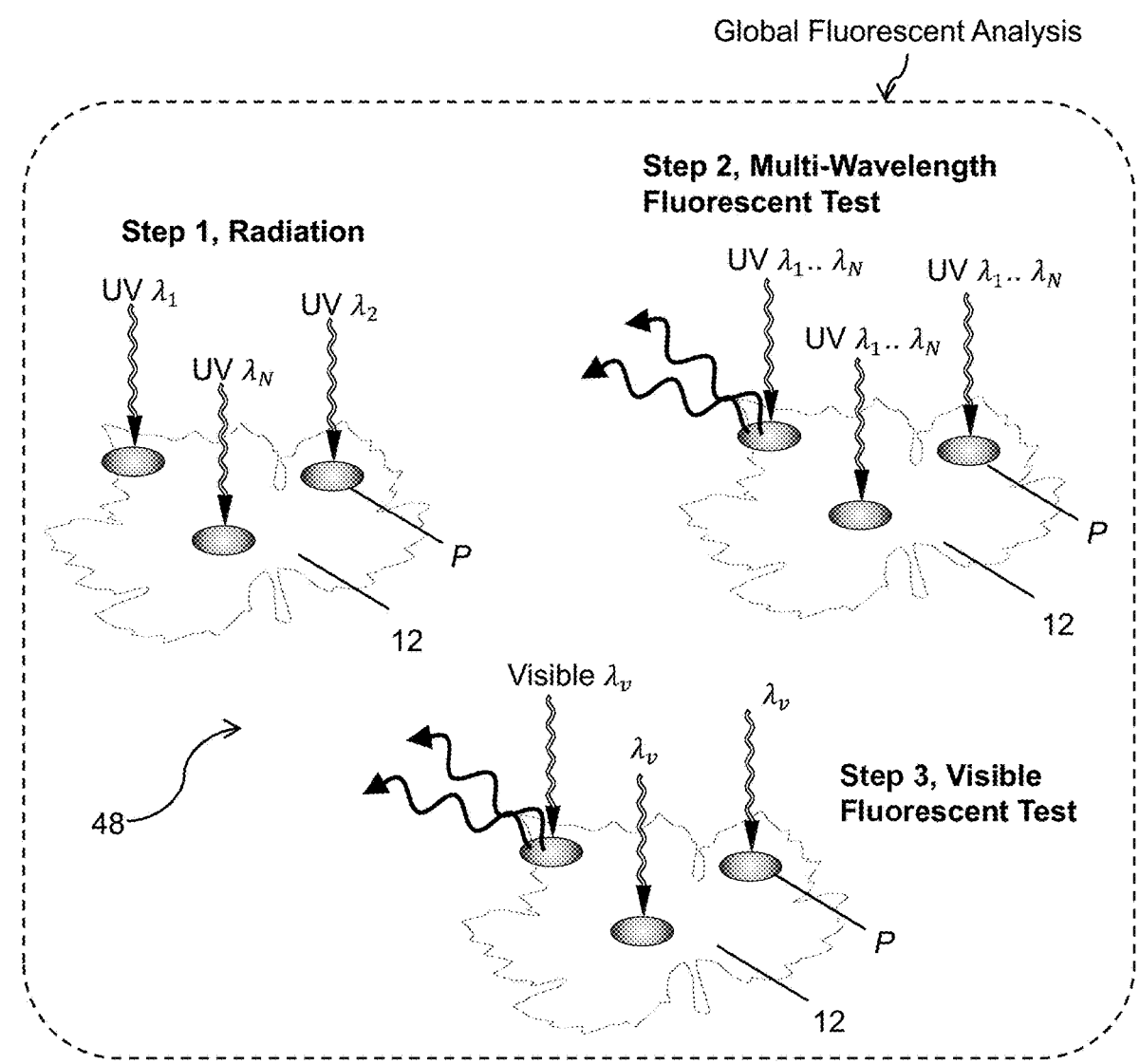
FIG. 6 shows details of a fluorescent analysis according to one embodiment that can be utilized in the fluorescent analysis depicted in FIG. 5.

FIG. 6 shows details of a fluorescent analysis according to one embodiment that can be utilized in one of the various embodiments described herein. In particular, FIG. 6 describes the steps of a fluorescent analysis 48 that can be performed with the spot irradiation of the object 12 such as a plant. In one embodiment, in a first step, a set of locations P on the plant can be irradiated by a single ultraviolet radiation source such that each location receives a different wavelength of the ultraviolet radiation from the source. In the second step, the locations P can be irradiated with a set of different ultraviolet radiation sources. In one embodiment, each of the different ultraviolet radiation sources can irradiate a respective location with multiple wavelengths of ultraviolet radiation. To this extent, each location can receive a different wavelength of the ultraviolet radiation from the single ultraviolet radiation source used in step 1. The controller 20 (FIG. 1) can record the fluorescent signals obtained from a fluorescence sensor for each of the locations after irradiation of the different wavelengths of the ultraviolet radiation by the multiple excitation sources. The fluorescence data generated from step 2 can give further information on the chemical modification of a plant surface. For example, the information can detail the type of chemical components present at the plant surface. In addition, the information can indicate the amount of the chemical components present at the plant surface via a thickness of any newly formed film of chemical materials such as flavonoids.

The next step of the global fluorescent analysis depicted in FIG. 6 can include irradiating the set of locations P on the plant with visible light sources. The controller 20 can record the fluorescent signals obtained from a fluorescence sensor for each of the locations after irradiation by the visible light sources. The controller 20 can then use these fluorescent signals with those generated from the ultraviolet radiation sources to determine a ratio of fluorescent intensity like that depicted in FIG. 5. As mentioned above, the ratio of fluorescent intensity between the fluorescent signals of the ultraviolet radiation and visible radiation can be used to ascertain various information that pertains to the growth of the plant. In addition, this information can be used to determine the optimal settings that can be used for irradiating a set of locations of a plant in an operational treatment mode including wavelength, intensity, dosage, duration, etc.

Figure 7:
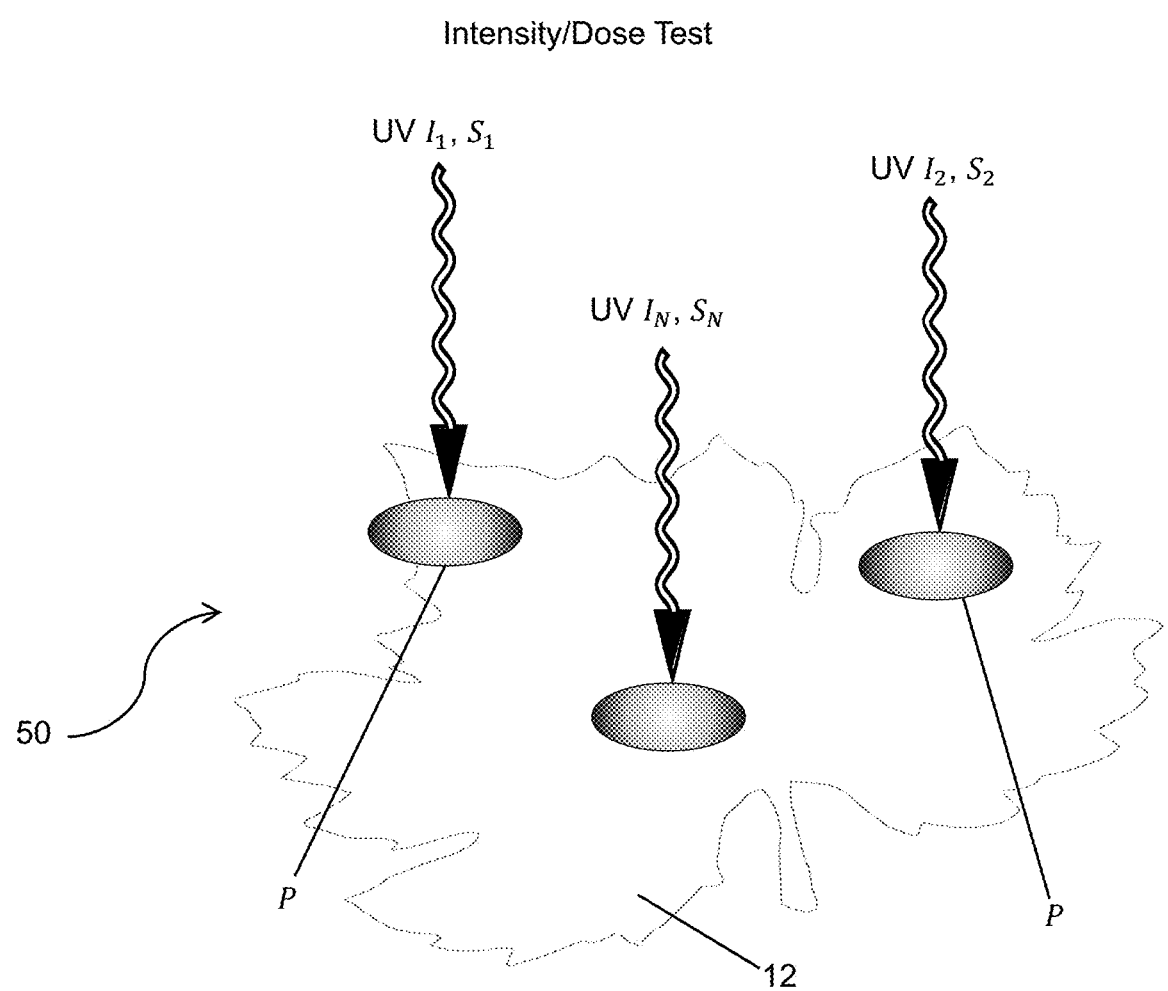
FIG. 7 shows an alternative fluorescent analysis that can be performed in the fluorescent analysis depicted in FIG. 6 in which the intensity and duration of the radiation irradiating the object is varied between different regions according to an embodiment.

FIG. 7 shows an alternative fluorescent analysis 50 that can be performed in the flow chart of FIG. 5 in place of the fluorescent analysis depicted in FIG. 6. In this embodiment, instead of irradiating the set of locations P with different wavelengths of ultraviolet radiation as depicted in step 1 of FIG. 5, these locations can be irradiated with varying intensities and durations of the radiation. Irradiating the set of locations P with varying intensities and durations of ultraviolet radiation affords determination of the optimal dose of radiation on affecting the plant leaf or a plant fruit. Although not illustrated, the embodiment depicted in FIG. 7 could utilize steps two and three shown in FIG. 6, to generate the same information that pertains to plant growth and optimal irradiation settings in an operational treatment mode for growing plants in all stages of plant growth under a variety of environmental conditions.

Figure 8:
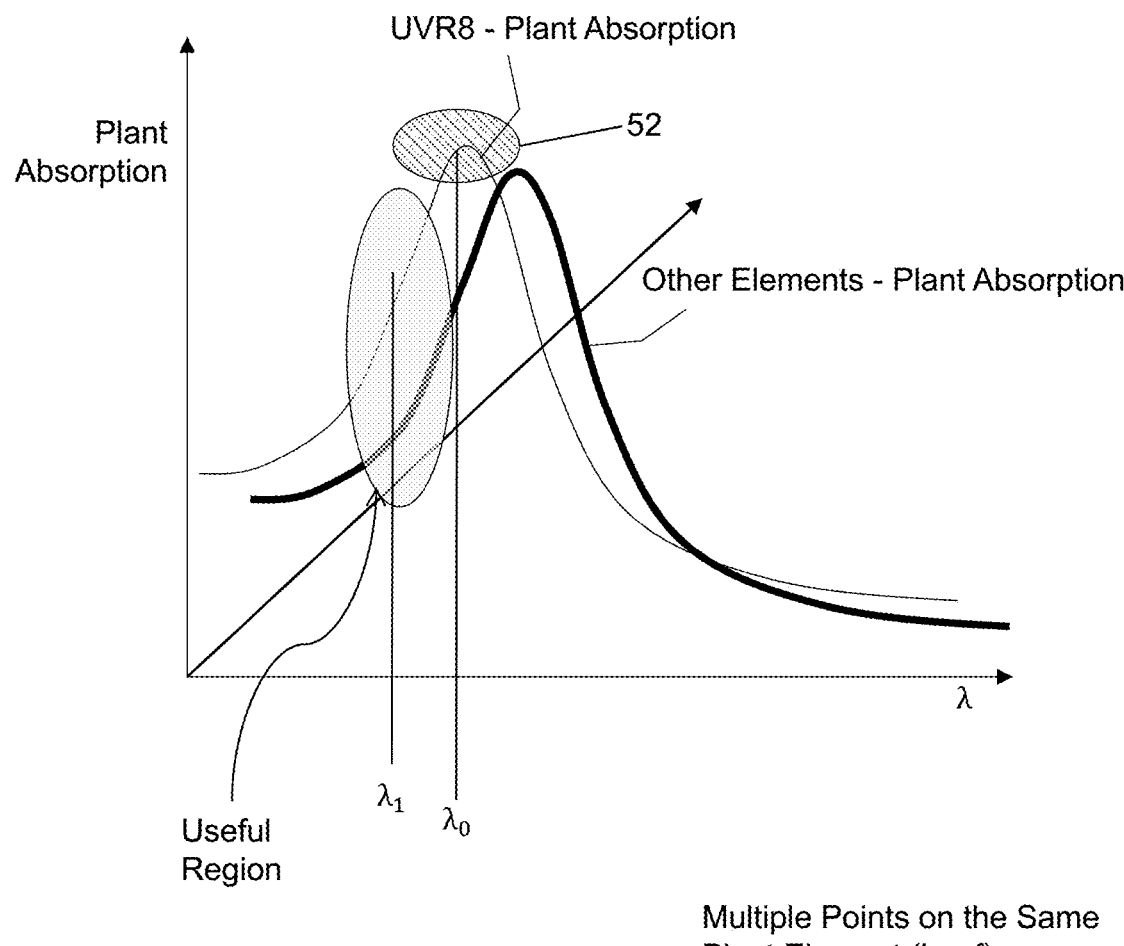
FIG. 8 illustrates an example showing the effect that the absorption of radiation can have on different elements of a light sensitive object such as a plant, and how balancing that effect on all of the elements can be used to find the optimal irradiation settings for irradiating the plant according to an embodiment.
Figure 8:
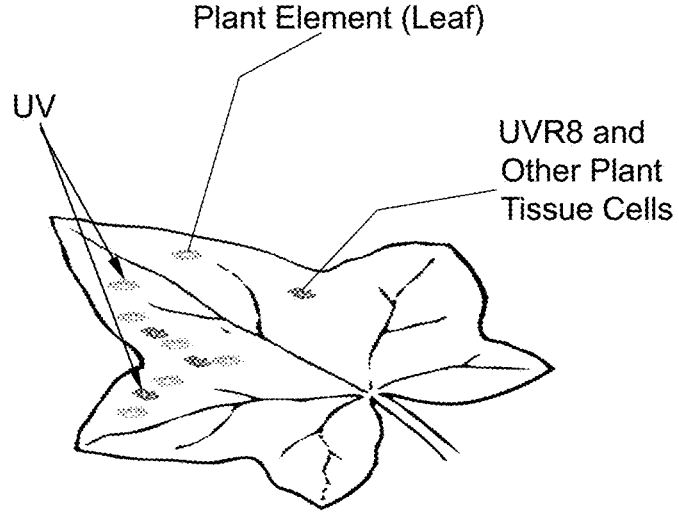

FIG. 8 illustrates an example showing the effect that the absorption of radiation can have on different elements of a light sensitive object 12 such as a plant, and how balancing that effect on all of the elements can be used to find the optimal irradiation settings for irradiating the plant according to an embodiment. It is understood that there are a multiple of different elements within a plant that effect its growth and development and that are sensitive to radiation. UVR8, Cryptochrome, Beta-Carotene, Chlorophyll A, Chlorophyll B, Phycoeryththrin, Phycocyanin, and Phytochrome are a non-exhaustive list of elements in a plant that effect growth and development and that are sensitive ultraviolet radiation. As an example, FIG. 8 shows a plot of the plant absorption spectra of these elements. In particular, FIG. 8 show a plant absorption spectra for UVR8, which as noted above, is an ultraviolet sensing protein found in plants that generally has a positive effect on plant growth and development depending on the amount of absorbed ultraviolet radiation. FIG. 8 also shows a plant absorption spectra for the other above-noted elements (i.e., Cryptochrome, Beta-Carotene, Chlorophyll A, Chlorophyll B, Phycoeryththrin, Phycocyanin, and Phytochrome).

From the perspective of plant growth and development, it is generally understood that radiation absorption by UVR8 is desirable, while absorption of the other elements might be less desirable or not desirable at all. An assessment of the effect that radiation will have on these other elements will ultimately depend on the element. Nevertheless, for purposes of this embodiment, it is assumed that the plant absorption spectra of UVR8 will have the stronger effect on the growth and development of a plant than the other elements. As a result, values for the parameters used to generate the plant absorption curve will be weighted higher in comparison to those associated with the other elements in determination of optimal irradiation settings.

In one embodiment, an effective wavelength λ setting for use in an operational treatment mode can be optimized to coincide with the absorption peak area of UVR8 which is designated by reference element 52, which has a wavelength of $\lambda_O$. However, a wavelength of $\lambda_O$ may be suboptimal if the absorption by the other elements is high at that wavelength. As shown in FIG. 8, the wavelength of the absorption of the other elements is relatively high, and as a result, a wavelength of $\lambda_O$, may not be a desirable setting as it can have somewhat of a deleterious effect on the plant. FIG. 8 shows a more useful region in the absorption curves designated by reference element 54 where the absorption of UVR8 is relatively high, while the absorption of the other elements is relatively low. FIG. 8 shows that the useful region 54 can be characterized with a wavelength of $\lambda_1$. As used herein, the term "relatively high" can mean absorption that is at least 50% of the absorption at the peak, while the term "relatively low" can mean absorption that is less than 50% of the absorption at the peak.

In general, an optimized wavelength from the absorption by the UVR8 and the other elements can be determined by constructing cost functional criteria that balances both the benefits of having high absorption by UVR8 and the penalty associated with the "undesirable absorption" by the other elements. With regard to the example illustrated in FIG. 8, such a cost functional criteria would lead to the optimal wavelength $\lambda_1$, which is different from the absorption peak wavelength $\lambda_1$. As shown in FIG. 8, wavelength $\lambda_1$ still yields a relatively high absorption for UVR8, and a relatively lower absorption by other elements. With the optimized wavelength identified, other irradiation settings can be specified that correspond with this parameter such as intensity, dosage, duration, and the like. In this manner, the irradiation settings can be used in an operational treatment mode to grow and develop plants over a variety of environmental conditions under different growth periods to attain desirable flavonoid and antioxidant production.

Figure 9:
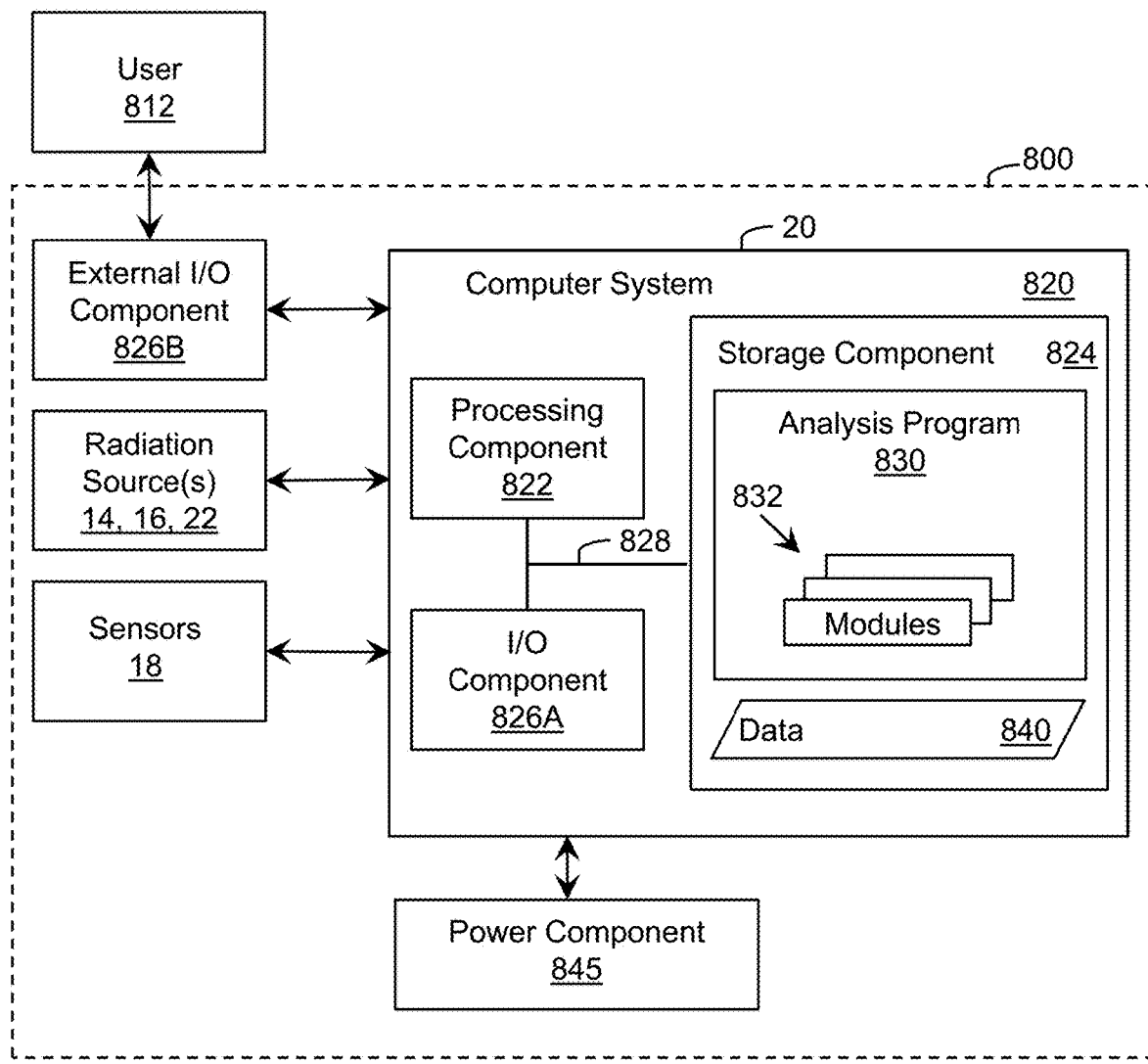
FIG. 9 shows a schematic block diagram representative of an overall processing architecture of a light exposure control system for irradiating a light sensitive object according to an embodiment.

Referring now to FIG. 9, there is a schematic block diagram representative of an overall processing architecture of a system 800 for a light exposure control system that can be used to irradiate a light sensitive object. In this embodiment, the architecture 800 is shown including the radiation sources 14, 16, 22 and the sensors 18 for the purposes of illustrating the interaction of all of the components that can be used to provide a light exposure system for irradiating a light sensitive object.

As depicted in FIG. 9 and described herein, the system 800 can include a controller 20. In one embodiment, the controller 20 can be implemented in the form of a control unit embodying a computer system 820 including an analysis program 830, which makes the computer system 820 operable to manage the radiation sources 14, 16, 22 and the sensors 18 in the manner described herein. In particular, the analysis program 830 can enable the computer system 820 to operate the radiation sources 14, 16, 22 to direct radiation towards the object and process data obtained during operation which is stored as data 840. The computer system 820 can individually control each source 14, 16, 22 and sensor 18 and/or control two or more of the sources and the sensors as a group. Furthermore, the radiation sources can emit radiation of substantially the same wavelength or of multiple distinct wavelengths.

In an embodiment, during an initial period of operation, the computer system 820 can acquire data from at least one of the sensors 18 regarding one or more attributes of the light exposure control system and generate data 840 for further processing. The computer system 820 can use the data 840 to control one or more aspects of the radiation generated by the radiation sources 14, 16, 22 during testing and operational modes.

Furthermore, one or more aspects of the operation of the radiation sources 14, 16, 22 can be controlled or adjusted by a user 812 via an external interface I/O component 826B. The external interface I/O component 826B can be used to allow the user 812 to selectively turn on/off the radiation sources 14, 16, 22.

The external interface I/O component 826B can include, for example, a touch screen that can selectively display user interface controls, such as control dials, which can enable the user 812 to adjust one or more of: an intensity, and/or other operational properties of the set of radiation sources 14, 16, 22 (e.g., operating parameters, radiation characteristics). In an embodiment, the external interface I/O component 826B could include a keyboard, a plurality of buttons, a joystick-like control mechanism, and/or the like, which can enable the user 812 to control one or more aspects of the operation of the set of radiation sources 14, 16, 22. The external interface I/O component 826B also can include any combination of various output devices (e.g., an LED, a speaker, a visual display), which can be operated by the computer system 820 to provide status information for use by the user 812. For example, the external interface I/O component 826B can include one or more LEDs for emitting a visual light for the user 812, e.g., to indicate a status of the irradiation of the samples. In an embodiment, the external interface I/O component 826B can include a speaker for providing an alarm (e.g., an auditory signal), e.g., for signaling that ultraviolet radiation is being generated or that an irradiation has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the sources and the sensors. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively. Illustrative aspects of the invention are further described in conjunction with the computer system 820. However, it is understood that the functionality described in conjunction therewith can be implemented by any type of monitoring and/or control system.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 9 can receive power from a power component 845. The power component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, etc.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A light exposure control device for irradiating an object having a light sensitive surface, comprising:
    a first set of radiation sources configured to irradiate the light sensitive surface of the object with visible radiation and infrared radiation;
    a second set of radiation sources configured to spot irradiate the light sensitive surface of the object in a set of predetermined locations with radiation having a range of wavelengths, wherein each predetermined location is smaller than the light sensitive surface of the object;
    a plurality of environmental condition sensors that detect conditions of the environment in which the object is located during irradiation by the first and second set of radiation sources; and
    a controller configured to control irradiation of the light sensitive surface of the object by the first and second set of radiation sources according to a plurality of predetermined optimal irradiation settings specified for various environmental conditions, wherein each predetermined location corresponds to a location on the light sensitive surface of the of the object determined to require supplemental irradiation with radiation having the range of wavelengths to induce a desired effect on the object, the controller adjusting irradiation settings of the first and second set of radiation sources as a function of the environmental conditions detected by the plurality of environmental condition sensors.

2. The device of claim 1, wherein the first set of radiation sources irradiate the object according to a predetermined schedule that follows an amount of daylight and darkness in a given day of a year, wherein the first set of radiation sources are operational to irradiate the object during daylight hours and inoperative during nighttime hours.

3. The device of claim 1, further comprising a set of fluorescent radiation sources configured to irradiate the object with radiation configured to induce fluorescence.

4. The device of claim 1, wherein the second set of radiation sources comprises a plurality of ultraviolet light emitting devices, each operating at a different peak wavelength, wherein each of the ultraviolet light emitting devices is configured to irradiate a location of the light sensitive object with supplemental irradiation beyond the irradiation provided by the first set of radiation sources.

5. The device of claim 4, wherein more than one of the ultraviolet light emitting devices are configured to irradiate a common location of the light sensitive object, wherein each ultraviolet light emitting device irradiates the common location at a different intensity of radiation.

6. The device of claim 1, wherein the plurality of environmental condition sensors comprises at least one of: a temperature sensor, a humidity sensor, a $CO_2$ sensor, a water sensor, or a nutrient sensor.

7. The device of claim 1, wherein the predetermined optimal irradiation settings of the first and second set of radiation sources comprises a combination of intensity, dosage, duration, wavelength, type of radiation, and pattern of radiation.

8. A light exposure control device for irradiating a plant, comprising:
a set of visible light and infrared radiation sources configured to irradiate a surface of the plant with visible radiation and infrared radiation;
a set of ultraviolet radiation sources configured to spot irradiate the surface of the plant in a set of predetermined locations with a target ultraviolet radiation having a range of wavelengths, wherein each predetermined location is smaller than the surface of the plant;
a plurality of environmental condition sensors that detect conditions of the environment in which the plant is located during irradiation by the set of visible light and infrared radiation sources and the set of ultraviolet radiation sources; and
a controller configured to control irradiation of the surface of the plant by the set of visible light and infrared radiation sources and the set of ultraviolet radiation sources according to a plurality of predetermined optimal irradiation settings specified for various environmental conditions, wherein each predetermined location corresponds to a location on the surface of the of the plant determined to require supplemental irradiation with radiation having the range of wavelengths to induce a desired effect on the plant, wherein the controller directs the set of ultraviolet radiation sources to irradiate the set of predetermined locations on the surface of the plant with a first radiation having a distinct wavelength of emitted radiation at a predetermined intensity and duration, and at a second radiation having a wavelength of emitted radiation at a predetermined intensity and duration that is different from the first radiation, wherein the first radiation and second radiation are configured to induce fluorescence in the irradiated set of predetermined locations.

9. A controlled growth environment, comprising the light exposure control device of claim 8, wherein the controlled growth environment is configured to control a plurality of plant growth parameters as a function of the conditions of the environment.

10. The controlled growth environment of claim 9, wherein the plurality of plant growth parameters comprises an amount of water provided to the plant, air temperature at a location of the plant, an amount of nutrients provided to the plant, and an amount of pesticides applied to the plant.

11. The device of claim 8, wherein the controller directs the set of visible light and infrared radiation sources and the set of ultraviolet radiation sources to irradiate the plant during different periods of plant growth, the different periods including a plant seedling period, a plant development period, a plant maturity period, plant blooming period, and a plant fruition period.

12. The device of claim 11, wherein the controller is configured to receive measurements from the plurality of environmental condition sensors at various times of the day during each of the different periods of plant growth.

13. The device of claim 8, wherein the controller directs the set of visible light and infrared radiation sources, and the set of ultraviolet radiation sources to irradiate the plant according to a predetermined irradiation pattern.

14. The device of claim 13, wherein the predetermined irradiation pattern comprises a first irradiation by the set of ultraviolet radiation sources, followed by second irradiation by the set of visible light and infrared sources, and a third irradiation by a plurality fluorescent radiation sources configured to irradiate the plant with radiation configured to induce fluorescence.

15. A method, comprising:
irradiating a light sensitive surface of an object with visible radiation and infrared radiation;
spot irradiating the light sensitive surface of the object in a set of predetermined locations with radiation having a range of wavelengths, wherein each predetermined location is smaller than the light sensitive surface of the object;
detecting conditions of the environment in which the object is located during the irradiation and spot irradiation; and
controlling the irradiation and spot irradiation of the light sensitive surface of the object according to a plurality of predetermined optimal irradiation settings specified for various environmental conditions, wherein each predetermined location corresponds to a location on the light sensitive surface of the of the object determined to require supplemental irradiation with radiation having the range of wavelengths to induce a desired effect on the object, the controlling including adjusting irradiation settings as a function of the environment conditions.

16. The method of claim 15, further comprising receiving measurements from a plurality of environmental condition sensors at various times of the day and adjusting the irradiation settings as a function of the measurements.

17. The method of claim 15, further comprising irradiating the light sensitive object with radiation configured to induce fluorescence.

18. The method of claim 17, further comprising irradiating and spot irradiating the light sensitive surface of the object according to a predetermined irradiation pattern.

19. The method of claim 18, wherein the predetermined radiation pattern comprises:
first spot irradiating the light sensitive surface of the object with ultraviolet radiation;

second irradiating the light sensitive surface of the object with visible radiation and infrared radiation; and third irradiating the light sensitive surface of the object with the radiation configured to induce fluorescence.

20. The method of claim 15, wherein the various environment conditions includes temperature, humidity, a presence of $CO_2$, and a presence of water.

* * * * *